United States Patent [19]

de Winter

[11] Patent Number: 4,515,606
[45] Date of Patent: May 7, 1985

[54] GAS SEPARATING AND VENTING FILTER

[75] Inventor: Dirk M. de Winter, Solana Beach, Calif.

[73] Assignee: Brunswick Corporation, Skokie, Ill.

[21] Appl. No.: 245,444

[22] Filed: Mar. 19, 1981

[51] Int. Cl.³ .................................................. B01D 19/00
[52] U.S. Cl. ........................................ 55/159; 55/178
[58] Field of Search ................ 55/16, 158, 159, 178, 55/185, 199; 128/214 R, 214 C, 214.2; 210/94, 321.1, 446

[56] References Cited

U.S. PATENT DOCUMENTS

| | | | |
|---|---|---|---|
| 3,295,297 | 1/1967 | Collins | 55/178 |
| 3,471,019 | 10/1969 | Trasen et al. | 210/94 |
| 3,523,408 | 8/1970 | Rosenberg | 55/159 |
| 3,631,654 | 1/1972 | Riely et al. | 55/159 |
| 3,650,093 | 3/1972 | Rosenberg | 55/159 |
| 3,701,433 | 10/1972 | Krakauer et al. | 128/214 C X |
| 3,778,973 | 12/1973 | Martinez | 55/199 |
| 3,795,558 | 3/1974 | Dabney et al. | 128/214 C X |
| 3,803,810 | 4/1974 | Rosenberg | 55/159 |
| 3,827,561 | 8/1974 | Serfass et al. | 210/180 |
| 3,834,124 | 9/1974 | Ichikawa | 55/159 |
| 3,891,416 | 6/1975 | Leonard et al. | 55/178 |
| 3,905,905 | 9/1975 | O'Leary et al. | 55/159 X |
| 3,993,062 | 11/1976 | Jess | 55/159 X |
| 4,004,587 | 1/1977 | Jess | 55/159 X |
| 4,009,714 | 3/1977 | Hammer | 128/214 C X |
| 4,013,072 | 3/1977 | Jess | 128/214 C |
| 4,030,495 | 6/1977 | Virag | 128/214.2 |
| 4,031,891 | 6/1977 | Jess | 128/214.2 X |
| 4,113,627 | 9/1978 | Leason | 128/214 R X |
| 4,142,523 | 3/1979 | Stegeman | 128/214 C X |
| 4,177,149 | 12/1979 | Rosenberg | 55/159 X |
| 4,188,948 | 2/1980 | Swinton | 55/159 X |
| 4,190,426 | 2/1980 | Ruschke | 55/185 |
| 4,238,207 | 12/1980 | Ruschke | 55/159 |
| 4,276,170 | 6/1981 | Vaillancourt | 55/159 X |
| 4,278,084 | 7/1981 | Pope, Jr. | 55/159 X |
| 4,294,594 | 10/1981 | Sloane, Jr. et al. | 55/199 X |
| 4,298,358 | 11/1981 | Ruschke | 55/185 |

FOREIGN PATENT DOCUMENTS 1221625  2/1971  United Kingdom ............... 55/159

Primary Examiner—Robert Spitzer
Attorney, Agent, or Firm—John G. Heimovics; John R. Hoffman

[57] ABSTRACT

A gas separating and venting filter is disclosed for separating gases and liquids and venting the gases in any position of the filter. A housing defines an interior chamber, with inlet and outlet means for the flow of liquid into and out of the chamber. A hydrophilic filter membrane extends along one major wall of the chamber, with longitudinally extending open-sided passageways in the one major wall facing the hydrophilic filter membrane and leading to the outlet means. The hydrophilic filter membrane is flexible for ballooning into the passageways in response to a build-up of pressure in the chamber to restrict and/or cut off the flow of liquid through the passageways. A hydrophobic filter membrane extends along substantially the entire length of an opposite major wall of the chamber between the inlet and outlet means for passing gas but not liquid therethrough. A plurality of spaced vent holes are formed in the opposite major wall for venting gas which has passed through the hydrophobic filter membrane.

9 Claims, 10 Drawing Figures

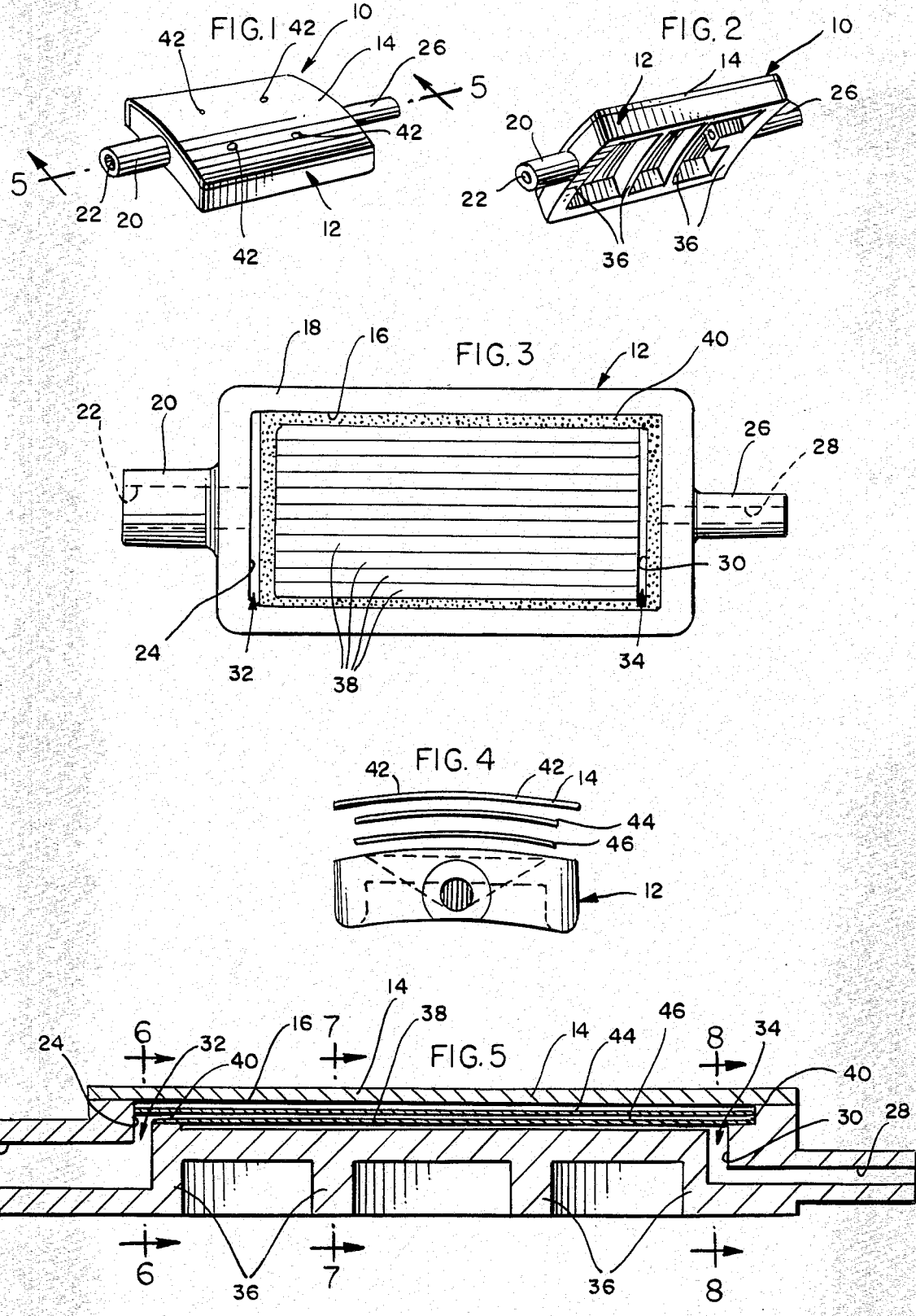

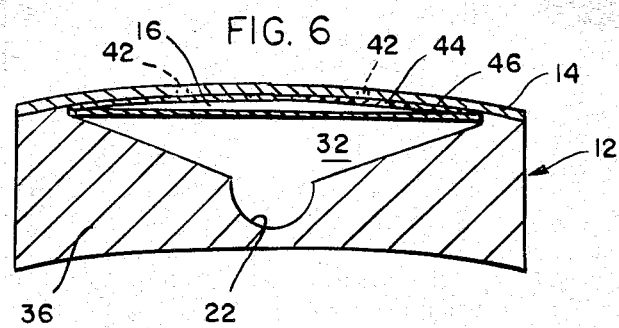
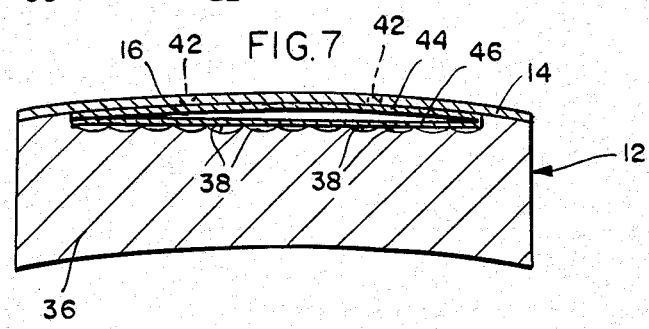
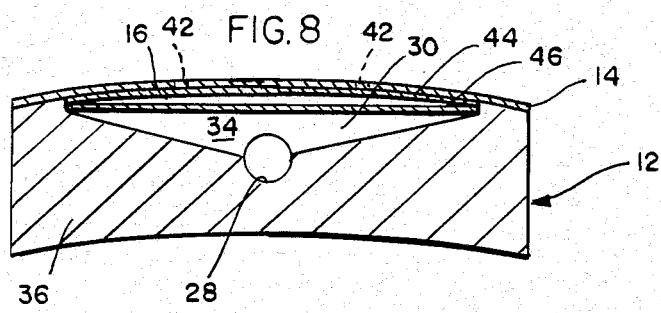
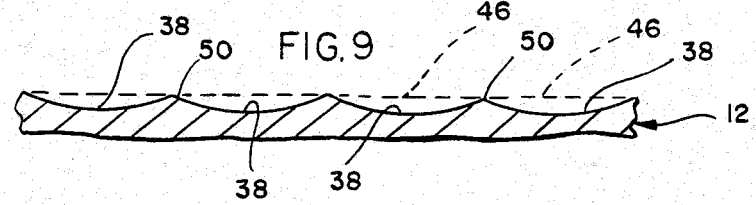
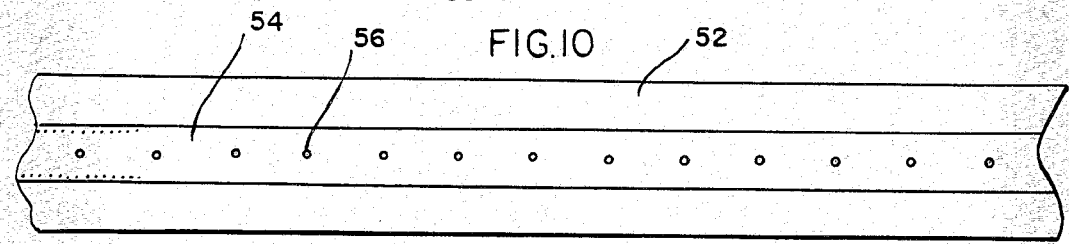

GAS SEPARATING AND VENTING FILTER

BACKGROUND OF THE INVENTION

This invention relates to liquid filters and particularly to filters which are capable of separating gases and liquids and of venting the gases. The invention specifically relates to filters of the character described which are capable of separating gas from liquid in fluids which are administered to a living patient.

The entrainment of gases in liquids and of liquids in gases are common problems which require apparatus to separate the gas from the liquid. This is particularly true in filters used for filtering blood, plasma, parenteral solution, or other fluid to a living patient, usually human. In addition to filtering out particulate matter and potentially harmful micro-organisms, it is extremely important that no entrained gas remain in the fluid so as to eliminate any hazard of embolism from air or gas reaching the patient. However, there are various continuing problems in using such filters in the medical field.

One problem involves the cost of such filters which, itself, is a continuing nemesis of the medical industry. It is desirable to provide relatively inexpensive instruments, such as syringes, or the like, which are sufficiently inexpensive to manufacture that they are disposable after use with an individual patient. This avoids costly manpower and equipment to continuously clean and re-use the medical equipment. This is equally applicable for intravenous filters, for instance. Heretofore, gas separating and venting filters have incorporated hydrophilic and hydrophobic subassemblies which greatly increase the cost of such filters.

Another problem concerns the use of such filters on a patient so that the filters are completely operative in any position or orientation. For instance, it is desirable to utilize the filters in-line with the flow of fluid and which may be directly or indirectly attached to a movable body member of a patient. Movement of the patient effects different orientations of the filter and the filter must be operative in any position. Without such capabilities, gas bubbles accumulate within the filter, touching the hydrophilic filter element and thereby inhibiting the flow of liquid therethrough.

A further problem concerns the build-up of pressure in the system and on the fluid flowing through the filter to a patient. This can harm the patient. Heretofore, pressure build-ups have been compensated for by mechanisms extraneous of the filter to avoid excessive pressures on the fluid, either before or after the fluid passes through the filter. It would be highly desirable to provide an automatic pressure compensating means directly in the filter, particularly without increasing the cost or size of the filter itself.

The present invention is directed to providing a new and improved filter of the character described which is directed to solving these varying problems in a very simple and inexpensive gas separating and venting filter.

SUMMARY OF THE INVENTION

The present invention, therefore, is directed to a new and improved gas separating and venting filter that is capable of separating gases and liquids and of venting the gases from the filter, particularly for use in filtering blood, plasma, parenteral solution, or other fluid, for administration to a living patient.

One object of the present invention is to provide a filter of the character described which is very inexpensive to manufacture and therefore can be used as a disposable medical implement.

Another object of the invention is to provide a gas separating and venting filter that is capable of separating gases and liquids and of venting the gases in any position of the filter.

A further object of the invention is to provide a filter of the character described which has built-in means for automatically compensating for the build-up of pressure in-line with the liquid flow through the filter.

In the exemplary embodiment of the invention, a gas separating and venting filter is provided with a molded plastic housing having walls defining an interior chamber. The walls include a pair of oppositely facing major walls extending longitudinally between two end walls. Inlet means and outlet means are provided in the opposite end walls of the housing for the flow of liquid into and out of the chamber. The housing is fabricated of two simple molded plastic parts. One part has a longitudinally extending recess with one major wall defining the bottom of the recess, and with opposite ends of the recess having inlet and outlet ports defining the inlet and outlet means to and from the chamber. A second housing part comprises a cap sealed to the first housing part, closing the recess to define the interior chamber of the housing.

A flexible plastic hydrophobic filter membrane is ultrasonic welded about its periphery to the underside of the housing cap. A plurality of spaced vent holes are provided through the cap for venting gas which has passed through the hydrophobic filter membrane. The membrane covers substantially the entire inside of the cap so that the filter is operative in any position thereof.

A flexible plastic hydrophilic filter membrane is ultrasonic welded about its periphery to the major wall which defines the bottom of the recess in the second housing part. Fluid flows into the interior chamber of the housing between the two filter membranes.

A plurality of passageways are formed in the major wall of the second housing part beneath the hydrophilic filter membrane for passing liquid only therethrough to the outlet means. Each passageway is open-sided facing the hydrophilic filter membrane. The passageways extend generally parallel to each other and parallel to the membrane along the major wall leading toward the outlet means. Each passageway comprises a longitudinal cylindrical section of less than 180° and presenting a smooth concave surface facing the hydrophilic filter membrane. The composite depth of the passageways is within the elastic limits of the flexible hydrophilic membrane. Thus, the membrane is capable of ballooning into the passageways in response to a build-up of pressure in the chamber to restrict the flow of liquid through the passageways, until the membrane ultimately engages the concave sides of the passageways under extreme pressure to completely shut off the flow of liquid to the outlet means.

Other objects, features and advantages of the invention will be apparent from the following detailed description taken in connection with the accompanying drawings.

DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

FIG. 1 is a top perspective view of the filter of the present invention;

FIG. 2 is a bottom perspective view of the filter;

FIG. 3 is a top plan view of the filter, with the housing cap and filter membranes removed to illustrate the interior of the bottom housing part;

FIG. 4 is an exploded end elevational view of the filter, illustrating the two housing parts and two filter membranes thereof;

FIG. 5 is a vertical sectional view, on an enlarged scale, of the filter taken generally along the line 5—5 of FIG. 1;

FIG. 6 is a vertical sectional view taken generally along the line 6—6 of FIG. 5;

FIG. 7 is a vertical sectional view taken generally along the line 7—7 of FIG. 5;

FIG. 8 is a vertical sectional view taken generally along the line 8—8 of FIG. 5;

FIG. 9 is a fragmented sectional view, on an enlarged scale, through the passageways underlying the hydrophilic filter membrane of the present invention; and FIG. 10 is a plan view of a continuous length of hydrophobic filter and venting means of another embodiment of the invention.

DETAILED DESCRIPTION OF THE INVENTION

The invention is disclosed herein in the form of a gas separating and venting filter, generally designated 10, that is capable of separating gases and liquids and of venting the gases in any position of the filter. To that end, the following specification will describe the filter using such terms as "vertical", "horizontal", "above", "below", as referring only to the depiction of the filter shown in the drawings. Consequently, these terms are not intended to be limiting in any nature but only to facilitate the description of the filter in relation to the drawings, it being an object of the invention to provide such a filter which is operative in any position.

Referring to the drawings in greater detail, and first to FIGS. 1–5, filter 10 includes a housing which is fabricated of two parts. One part, generally designated 12, forms the principal portion of the housing including the interior chamber thereof, and hereafter will be called the housing base. A second part 14 forms a cap for the base for sealing engagement therewith to define a closed chamber therewithin. Both parts are fabricated of molded plastic material.

Base 12 is formed with a substantial, longitudinally extending recess 16 which is bounded by an upwardly facing peripheral surface 18. Cap 14 is sealed to surface 18 to define an interior chamber of the housing provided by recess 16. A tubular inlet 20 has a through bore 22 for the flow of liquid into the chamber through an end wall 24 thereof. An outlet 26 has a through bore 28 for the flow of liquid out of the chamber through an end wall 30. As best seen in 3, 5 and 6, a generally triangularly shaped interior passage, generally designated 32, communicates between inlet bore 22 and chamber 26 adjacent end wall 24. As best seen in FIGS. 3, 5 and 8, a generally triangularly shaped passage, generally designated 34, communicates between outlet bore 28 and chamber 16 adjacent end wall 30. As best seen in FIGS. 2 and 5, a plurality of cross ribs 36 are molded integral with base 12 on the bottom thereof for strengthening purposes. Lastly, it can be seen in FIGS. 2, 4 and 6–8, that the bottom of the base defined by ribs 36 is upwardly concave for mating with the contour of a patient's limb or other body part.

An important feature of the invention, which will be described in greater detail hereinafter, comprises the formation of passageways 38 on a major longitudinal wall of base 16 on the interior thereof at the bottom of recess 16. A peripheral surface 40 (FIG. 3) surrounds the passageways for heat sealing a hydrophilic filter membrane thereto, as described hereinafter. It also can be seen in FIG. 3 that passageways 38 communicate with transverse triangular passage 30 leading to outlet bore 28, but the passageways do not communicate directly with transverse triangular passage 30 in communication with inlet bore 22.

Housing part 14 has a plurality of vent holes 42 for venting gas from the interior of the housing defined by chamber 16. As seen in FIG. 1, four vent holes are shown, but it is to be understood that any number, particularly greater than four, are contemplated to insure venting of the gases in any position of the filter so that gas bubbles are not entrapped within the housing.

Referring to FIGS. 4–8, a plastic hydrophobic filter membrane 44 is disposed between the inlet and outlet ends of the housing for passing liquid only therethrough. The hydrophobic filter membrane is ultrasonic sealed to the underside of cap 14 substantially along the entire length and width thereof so as to surround all of the vent holes 42 and permit gases to pass through the membrane and be vented from the filter through the holes in any position of the filter. The filter, being flexible, will move into and out of engagement with the underside of cap 14 as determined by the amount of gas passing therethrough. For instance, hydrophobic filter membrane 44 is shown spaced from the underside of cap 14 somewhat exagerated to further the illustration. A preferred form of sealing the periphery of membrane 44 to the underside of cap 14 is by ultrasonic welding.

A plastic hydrophilic filter membrane 46 is heat sealed, as by ultrasonic welding, to the peripheral surface 40 at the bottom of chamber 16 within base 12. Thus, the hydrophilic filter membrane completely covers passageways 38 which lead to the triangularly shaped transverse passage 34 communicating with outlet bore 28.

Referring to FIGS. 3, 7 and 9, an important feature of the invention is the size and configuration of passageways 38 beneath hydrophilic filter membrane 46. More particularly, as seen in FIG. 3, the passageways extend longitudinally substantially along the entire length of hydrophobic filter membrane 46. As seen in FIGS. 7 and 9, each passageway is open-sided facing the filter membrane and comprises a longitudinal cylindrical section of less than 180°. This presents a smooth concave surface of each passageway facing the membrane. The longitudinal edges 50 of the passageways define a mutual juncture between the passageways. The composite depth of all of the passageways is such as to be within the elastic limits of flexible hydrophobic filter membrane 46. Thus, the flexible membrane is capable of ballooning into the passageways in response to a build-up of pressure in the chamber to restrict the flow of liquid through the passageways by effectively reducing the cross-sectional dimensions of the passageways. If the pressure build-up is excessive, the membrane will flex until it ultimately engages the concave surfaces of the passageways to completely shut off the flow of liquid to passage 34 and outlet port 28. Thus, it can be seen that a self-contained, self-limiting underdrain is provided beneath hydrophilic membrane 46 which automatically adjusts for and regulates any pressure build-up in the in-line flow of liquid through the filter.

It can be seen from the above description of the filter of the present invention, that liquid flows into the filter through inlet bore 22 and triangular transverse passage 32 to the space between hydrophobic and hydrophilic filter membranes 44 and 46, respectively. At this point, any gases entrained in the liquid will pass through hydrophobic filter membrane 44 and out through vent holes 42 in cap 14. The gases are precluded from passing through hydrophilic filter member 46. The gasless liquid proceeds to pass through hydrophilic membrane 46, through passageways 38, into triangular transverse passage 34 and out through outlet bore 28. The flexibility of hydrophilic membrane 46 effectively accommodates any build-up of pressure in chamber 16 by means of its ballooning capabilities into the concave passageways. Excessive pressure, in fact, can cause the membrane to completely shut off the flow of fluid should the membrane engage the concave bottom surfaces of the passageways. It can be seen that this novel omni-directional filter, with its self-limiting pressure accommodating means, is fabricated of only two housing parts and two filter membranes, resulting in a very inexpensive unit which can be used for disposable, single-use applications.

Referring to FIG. 10, a novel means is shown for fabricating a continuous hydrophilic filter assembly of an alternate embodiment of the invention. In this assembly, a continuous strip 52 of plastic membrane material is provided. The strip has a length of filter material 54 centrally thereof and continuously therealong. The filter itself has a plurality of miniature apertures 56 for the passage of gases therethrough. This hydrophobic filter strip can be used from a continuous supply thereof and cut to any length or size for use with filter 10 of the present invention by simply cutting an appropriate section and ultrasonic welding that section to the underside of cap 14 of the filter. This continuous fabrication of the filter sections further enhances the simplicity and reduces the cost of the overall filter.

It will be understood that the invention may be embodied in other specific forms without departing from the spirit or central characterisitics thereof. The present examples and embodiments, therefor, are to be considered in all respects as illustrative and not restrictive, and the invention is not to be limited to the details given herein.

What is claimed is:

1. A gas separating and venting filter that is capable of separating gases and liquids and of venting the gases from the filter, comprising:
   a housing having walls defining an interior chamber, with inlet means in the housing for the flow of liquid into said chamber, and outlet means in the housing downstream of said inlet means for the flow of liquid out of said chamber;
   hydrophobic filter means adjacent one wall of said chamber between said inlet means and said outlet means for passing gas but not liquid therethrough, with vent means for venting gas which has passed through said hydrophobic filter means;
   a flexible hydrophobic filter membrane along a second wall of said chamber for passing liquid only therethrough; and
   at least one passageway in said second wall extending generally parallel to and along said filter membrane and leading toward said outlet means, said at least one passageway having an open side along its length facing said membrane, and an opposite side defining a smooth surface engageable by the membrane under pressure, and the passageway having a depth within the elastic limits of said flexible membrane, whereby the flexible membrane balloons into the passageway in response to a buildup of pressure in said chamber to restrict the flow of liquid through the passageway, until the membrane ultimately engages the smooth surface of said opposite side of the passageway under extreme pressure to completely shut off the flow of liquid to said outlet means.

2. The filter of claim 1 wherein said passageway has a concave cross-section generally perpendicular to the plane of said membrane.

3. The filter of claim 2 wherein said cross-section is that of a smooth longitudinal section of a cylinder.

4. The filter of claim 1 wherein said membrane is heat sealed to said second wall about said passageway.

5. The filter of claim 1 wherein said membrane is ultrasonic welded to said second wall about the periphery of the membrane.

6. The filter of claim 1 including a plurality of said open-sided passageways extending generally parallel to each other and parallel to said membrane along said second wall.

7. The filter of claim 6 wherein said passageways comprise longitudinal cylindrical sections presenting smooth concave surfaces facing said membrane.

8. The filter of claim 7 wherein said passageways comprise longitudinal cylindrical sections of less than 180°, with the longitudinal edges of each passageway defining a mutual juncture with the adjacent passageway.

9. A gas separating and venting filter that is capable of separating gases and liquids and of venting the gases from the filter, comprising:
   a housing having walls defining an interior chamber, with inlet means in the housing for the flow of liquid into said chamber, and outlet means in the housing downstream of said inlet means for the flow of liquid out of said chamber;
   hydrophobic filter means adjacent one wall of said chamber between said inlet means and said outlet means for passing gas but not liquid therethrough, with vent means for venting gas which has passed through said hydrophobic filter means;
   a flexible hydrophilic filter membrane along a second wall of said chamber for passing liquid only therethrough; and
   a plurality of open-sided passageways in said second wall extending generally parallel to each other and parallel to and facing said filter membrane and leading toward said outlet means, each of said passageways comprising a longitudinal cylindrical section of less than 180° presenting a smooth concave surface facing said membrane, the composite depth of said passageways being within the elastic limits of said flexible membrane, whereby the flexible membrane balloons into the passageways in response to a build-up of pressure in said chamber to restrict the flow of liquid through the passageways, until the membrane ultimately engages the concave sides of the passageways under extreme pressure to completely shut off the flow of liquid to said outlet means.

* * * * *